United States Patent
Ito

(10) Patent No.: US 9,180,079 B2
(45) Date of Patent: Nov. 10, 2015

(54) SKIN EXTERNAL PREPARATION AND METHOD OF PRODUCING SAME

(75) Inventor: Naoko Ito, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 146 days.

(21) Appl. No.: 13/978,036

(22) PCT Filed: May 2, 2012

(86) PCT No.: PCT/JP2012/062076
§ 371 (c)(1),
(2), (4) Date: Jul. 2, 2013

(87) PCT Pub. No.: WO2012/153825
PCT Pub. Date: Nov. 15, 2012

(65) Prior Publication Data
US 2013/0287718 A1    Oct. 31, 2013

(30) Foreign Application Priority Data

May 12, 2011 (JP) ................................. 2011-107599

(51) Int. Cl.
| | | |
|---|---|---|
| *A61Q 19/00* | (2006.01) | |
| *A61Q 19/02* | (2006.01) | |
| *A61K 31/665* | (2006.01) | |
| *A61K 8/55* | (2006.01) | |
| *A61K 8/44* | (2006.01) | |
| *A61K 8/67* | (2006.01) | |

(52) U.S. Cl.
CPC ... *A61K 8/55* (2013.01); *A61K 8/44* (2013.01); *A61K 8/442* (2013.01); *A61K 8/676* (2013.01); *A61K 31/665* (2013.01); *A61Q 19/00* (2013.01); *A61Q 19/02* (2013.01)

(58) Field of Classification Search
CPC ......... A61Q 19/00; A61Q 19/02; A61K 8/44; A61K 8/55; A61K 8/676; A61K 31/665
See application file for complete search history.

(56) References Cited

U.S. PATENT DOCUMENTS

| | | | |
|---|---|---|---|
| 2006/0263399 A1 | 11/2006 | Yasuno et al. | |
| 2009/0203649 A1* | 8/2009 | Kato et al. | ................... 514/100 |

FOREIGN PATENT DOCUMENTS

| | | |
|---|---|---|
| EP | 0 875 514 A1 | 11/1998 |
| EP | 2 238 969 A1 | 10/2010 |
| JP | 10-298174 A | 11/1998 |
| JP | 2003-176217 A | 6/2003 |
| JP | 2005-187466 A | 7/2005 |
| JP | 2005-336156 A | 12/2005 |
| JP | 2007-262039 A | 10/2007 |
| JP | 2007-269668 A | 10/2007 |
| JP | 2008-13464 A | 1/2008 |
| JP | 2008-106035 A | 5/2008 |
| WO | 98/23152 A1 | 6/1998 |
| WO | 2005/034903 A1 | 4/2005 |

OTHER PUBLICATIONS

Sundram, Kalyana, Ravigadevi Sambanthamurthi, and Yew-Ai Tan. "Palm fruit chemistry and nutrition." Asia Pacific journal of clinical nutrition 12.3 (2003): 355-362.*
International Search Report for PCT/JP2012/062076 dated May 29, 2013.
Japanese Office Action (Notice of Allowance) dated Jan. 20, 2015 issued an application No. 2011-107599.

* cited by examiner

*Primary Examiner* — Abigail Fisher
*Assistant Examiner* — Daniel L Branson
(74) *Attorney, Agent, or Firm* — Sughrue Mion, PLLC

(57) ABSTRACT

A skin external preparation containing an ascorbic acid-2-phosphate derivative is characterized in that only a sodium ascorbic acid-2-phosphate-6-palmitate is formulated as the ascorbic acid-2-phosphate derivative, and the skin preparation further includes at least one betaine-type amphoteric surfactant selected from the group consisting of compounds represented by the following general formula (1) or (2) (wherein $R^1$ represents a linear or branched alkyl group of 6 to 30 carbon atoms, and $R^2$ represents a linear or branched alkyl group of 8 to 30 carbon atoms).

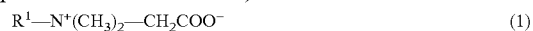

(1)

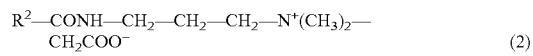

(2)

10 Claims, No Drawings

SKIN EXTERNAL PREPARATION AND METHOD OF PRODUCING SAME

TECHNICAL FIELD

The present invention relates to skin external preparation containing an ascorbic acid-2-phosphate derivative, and a method of producing the same.

BACKGROUND ART

Ascorbic acid (vitamin C) and various derivatives thereof are known to be compounds that exhibit effectiveness and efficacy in terms of skin whitening effects, antioxidative effects and collagen synthesis promotion effects and the like, and are therefore frequently added to pharmaceutical preparations, cosmetic materials and animal feed and the like.

Among ascorbic acid derivatives, ascorbic acid-2-phosphate derivatives in which the hydroxyl group at position 2 of ascorbic acid is converted to a phosphate ester are widely used due to their resistance to oxidation in air. Examples of known ascorbic acid-2-phosphate derivatives include ascorbic acid-2-phosphate and ascorbic acid-2-phosphate-6-higher fatty acid esters in which the hydroxyl group at position 6 of ascorbic acid-2-phosphate is esterified with a higher fatty acid such as palmitic acid. These ascorbic acid-2-phosphate derivatives are usually used in the form of salts. Typical examples of these salts include the sodium salt and magnesium salt of ascorbic acid-2-phosphate, and the sodium salts of ascorbic acid-2-phosphate-6-higher fatty acid esters.

Among the above derivatives, salts of ascorbic acid-2-phosphate-6-higher fatty acid esters, and particularly sodium ascorbic acid-2-phosphate-6-palmitate (hereinafter abbreviated as APPS), show considerable promise for application to skin preparations for external use such as cosmetic materials, because they are amphiphilic and therefore exhibit excellent compatibility with living organisms and their migration into biological tissues such as skin is rapid.

The advantages of APPS over other ascorbic acid derivatives are disclosed in Patent Document 1.

However, when salts of ascorbic acid-2-phosphate-6-higher fatty acid esters such as APPS are formulated as skin preparations for external use, decomposition tends to occur within the preparation, causing problems such as a change in the external appearance. This decomposition occurs mainly due to hydrolysis of the higher fatty acid bonded via an ester linkage to the hydroxyl group at position 6 of the ascorbic acid. As a result of this decomposition, higher fatty acid salts such as sodium palmitate that are insoluble in water are produced, and these appear as a precipitate within the preparation. In the case of a white turbid formulation such as a cream, this precipitate cannot be seen visually, but in a transparent lotion or beauty essence or the like, the precipitate appears as turbidity or sediment that causes a change in the external appearance of the product. Such a problem (caused by turbidity or sediment) tends to significantly occur in accordance with an increase in the length of higher fatty acid portions of ascorbic acid-2-phosphate-6-higher fatty acid esters, because such an increase raises the hydrophobicity of higher fatty acid salts generated by decomposition of the esters.

In response to these types of problems, various methods have been proposed for stabilizing the skin external preparation by adding other components to the ascorbic acid-2-phosphate-6-higher fatty acid ester salt.

For example, Patent Document 2 discloses a method of stabilizing a skin external preparation containing a salt of an ascorbic acid-2-phosphate-6-higher fatty acid ester by adding a water-soluble synthetic polymer compound such as a carboxy vinyl polymer and water to the preparation. It is stated that this method inhibits the decomposition and decrease of the salt of the ascorbic acid-2-phosphate-6-higher fatty acid ester within the skin external preparation, and can therefore suppress the generation of precipitates within the skin external preparation over time.

Patent Document 3 discloses a method of stabilizing a skin external preparation containing a salt of an ascorbic acid-2-phosphate-6-higher fatty acid ester by adding a polyhydric alcohol. It is stated that this method can suppress turbidity and the generation of precipitates within the skin external preparation over time.

Patent Document 4 discloses a method of stabilizing a skin external preparation containing a salt of an ascorbic acid-2-phosphate-6-higher fatty acid ester, wherein a polyglycerol fatty acid ester formed from a polyglycerol having an average polymerization degree of 8 to 12 and an unsaturated fatty acid residue of 14 to 22 carbon atoms, and a polyglycerol monofatty acid ester formed from a polyglycerol having an average polymerization degree of 2 to 6 and an unsaturated fatty acid residue of 14 to 22 carbon atoms are used as emulsifiers to form an emulsion having an average emulsion particle size of 1 to 200 nm. It is stated that this method inhibits the decomposition of the salt of the ascorbic acid-2-phosphate-6-higher fatty acid ester within the skin external preparation, thereby improving the storage stability and enabling better retention of a beautiful transparent or semi-transparent external appearance.

PRIOR ART DOCUMENTS

Patent Documents

[Patent Document 1]
Japanese Unexamined Patent Application, First Publication No. H 10-298174
[Patent Document 2]
Japanese Unexamined Patent Application, First Publication No. 2005-187466
[Patent Document 3]
Japanese Unexamined Patent Application, First Publication No. 2005-336156
[Patent Document 4]
Japanese Unexamined Patent Application, First Publication No. 2008-13464

DISCLOSURE OF INVENTION

Problems to be Solved by the Invention

However, in the case of methods such as that disclosed in Patent Document 2, wherein a water-soluble synthetic polymer compound is added to the preparation, although a certain APPS decomposition inhibitory effect is obtained, the preparation remains unstable, and is prone to problems such as a decrease in viscosity, precipitation or discoloration upon changes in the pH or addition of dissociative compounds such as sodium chloride or sodium citrate. Addition of a carboxy vinyl polymer increases the viscosity of the preparation and is therefore particularly effective in stabilizing the emulsion, but because a neutralization operation is performed by adding a strong alkaline agent such as potassium hydroxide or sodium hydroxide, decomposition of the APPS tends to proceed reasonably easily, and the precipitation and discoloration over time is quite marked.

In the case of methods such as that disclosed in Patent Document 3, wherein a polyhydric alcohol is added, heavy use of the polyhydric alcohol in an emulsion tends to cause a reduction in the viscosity of the emulsion and a destabilization of the preparation.

In the case of methods such as that disclosed in Patent Document 4, wherein a polyglycerol mono-fatty acid ester is added, addition of dissociative compounds such as sodium chloride or sodium citrate tends to destabilize the emulsion, and depending on the variety of other compounds added to the preparation, creaming may occur, thereby preventing use of the preparation in oil-free transparent lotions, meaning the types of formulations to which the preparation can be applied are limited.

Further, when formulations containing APPS are stored at low temperature, the solubility of the APPS decreases, which can cause precipitation of the APPS itself.

Precipitation not only alters the external appearance of the formulation, but can also cause a deterioration in the sensation felt when the skin external preparation is applied to the skin.

Against the type of background circumstances described above, the development of a skin external preparation that contains APPS, exhibits excellent formulation stability that enables turbidity and precipitation to be inhibited over time, and also provides an excellent sensation upon use has been keenly sought.

The present invention takes the above circumstances into consideration, with an object of providing a skin external preparation that contains APPS and exhibits excellent formulation stability, and a method of producing such a skin preparation.

Means to Solve the Problems

As a result of intensive research aimed at achieving the above object, the inventors of the present invention discovered that by formulating only APPS as an ascorbic acid-2-phosphate derivative in a skin external preparation, and then combining the APPS with a specific amphoteric surfactant, the above object could be achieved, and they were therefore able to complete the present invention.

The present invention includes the following aspects.

[1] A skin external preparation comprising an ascorbic acid-2-phosphate derivative, characterized in that only a sodium ascorbic acid-2-phosphate-6-palmitate is formulated as the ascorbic acid-2-phosphate derivative, and the skin external preparation further comprises at least one betaine-type amphoteric surfactant selected from the group consisting of compounds represented by a general formula (1) or (2) shown below:

(1)

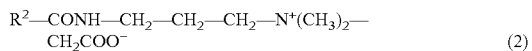

(2)

wherein $R^1$ represents a linear or branched alkyl group of 6 to 30 carbon atoms, and $R^2$ represents a linear or branched alkyl group of 8 to 30 carbon atoms.

[2] The skin external preparation according to [1], wherein at least one of the betaine-type amphoteric surfactant is a compound of the general formula (1) in which $R^1$ is a linear or branched alkyl group of 12 to 24 carbon atoms.

[3] The skin external preparation according to [1], wherein at least one of the betaine-type amphoteric surfactant is a compound of the general formula (2) in which $R^2$ is a linear or branched alkyl group of 12 to 24 carbon atoms.

[4] The skin external preparation according to any one of [1] to [3], wherein a formulating amount of the sodium ascorbic acid-2-phosphate-6-palmitate is within a range from 0.01 to 10% by mass, relative to a total mass of the skin external preparation.

[5] The skin external preparation according to any one of [1] to [4], wherein an amount of the betaine-type amphoteric surfactant is within a range from 0.1 to 10% by mass, relative to a total mass of the skin external preparation.

[6] The skin external preparation according to any one of [1] to [5], wherein a pH of the skin external preparation is within a range from 6.5 to 7.5.

[7] The skin external preparation according to any one of [1] to [6], wherein the skin external preparation is a cosmetic material.

[8] A method of producing a skin external preparation comprising an ascorbic acid-2-phosphate derivative, the method comprising:

formulating: only a sodium ascorbic acid-2-phosphate-6-palmitate as the ascorbic acid-2-phosphate derivative; and at least one betaine-type amphoteric surfactant selected from the group consisting of compounds represented by a general formula (1) or (2) shown below:

(1)

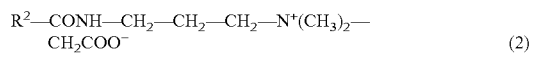

(2)

wherein $R^1$ represents a linear or branched alkyl group of 6 to 30 carbon atoms, and $R^2$ represents a linear or branched alkyl group of 8 to 30 carbon atoms.

[9] The method according to [8], wherein the sodium ascorbic acid-2-phosphate-6-palmitate is formulated in an amount of 0.01 to 10% by mass, relative to a total mass of the skin external preparation.

[10] The method according to [8], wherein the betaine-type amphoteric surfactant is formulated in an amount of 0.1 to 10% by mass, relative to a total mass of the skin external preparation.

Effect of the Invention

The present invention is able to provide a skin external preparation which contains APPS and exhibits excellent formulation stability.

MODES FOR CARRYING OUT THE INVENTION

Ascorbic Acid-2-Phosphate Derivative

First is a description of the APPS used in the present invention.

APPS is a compound represented by a chemical formula shown below. In other words, APPS is a compound in which phosphoric acid is bonded via an ester linkage to a hydroxyl group bonded to a carbon atom at position 2 of ascorbic acid, palmitic acid is bonded via an ester linkage to a hydroxyl group bonded to a carbon atom at position 6 of the ascorbic acid, and hydrogen atoms are dissociated from two hydroxyl groups bonded to a phosphorus atom within the phosphate group and a hydroxyl group bonded to a carbon atom at position 3 of the ascorbic acid to form a trisodium salt.

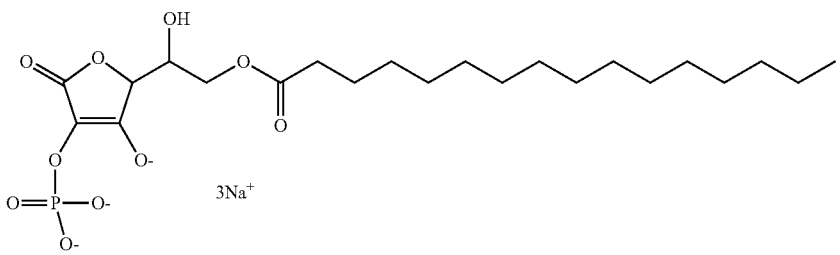 [SMILES: CCCCCCCCCCCCCCCC(=O)OCC(O)C1OC(=O)C(OP(=O)([O-])[O-])=C1[O-]]

The formulating amount of the APPS, relative to the total mass of the skin external preparation, is preferably within a range from 0.01 to 10% by mass, and more preferably from 0.5 to 5% by mass. Provided the amount is at least 0.01% by mass, the migration of the APPS into the skin occurs rapidly when the skin external preparation according to the present invention is applied to the skin, and the effectiveness and efficacy desired of the skin external preparation can be satisfactorily realized. Even if the formulating amount of the APPS exceeds 10% by mass, a corresponding increase in effect is usually not obtained.

In the skin external preparation of the present invention, only APPS is formulated as an ascorbic acid-2-phosphate derivative. In other words, when producing the skin external preparation of the present invention, only APPS is formulated as an ascorbic acid-2-phosphate derivative, and other ascorbic acid-2-phosphate derivatives besides APPS are not formulated. If other ascorbic acid-2-phosphate derivatives besides APPS are formulated in combination with the APPS, then decomposition of the APPS tends to be accelerated, the formulation stability deteriorates, and discoloration and precipitation become more likely. In particular, if sodium ascorbic acid-2-phosphate is formulated in combination with the APPS, then discoloration becomes a significant problem, whereas if magnesium ascorbic acid-2-phosphate is formulated in combination with APPS, then a magnesium salt of APPS tends to be produced, resulting in accelerated precipitation.

Examples of these other ascorbic acid-2-phosphate derivatives besides APPS include ascorbic acid-2-phosphate and salts thereof, and ascorbic acid-2-phosphate-6-higher fatty acid esters besides APPS and salts thereof. Examples of the salts include sodium salts, magnesium salts, and sodium-magnesium salts. Examples of the higher fatty acid in the ascorbic acid-2-phosphate-6-higher fatty acid esters besides APPS include fatty acids of 8 to 22 carbon atoms except for palmitic acid.

In the skin external preparation, the APPS may decompose to form palmitic acid and ascorbic acid-2-phosphate. Accordingly, the skin external preparation according to the present invention may include small amounts of ascorbic acid-2-phosphate or salts thereof over time, even though these compounds are not formulated at the time of production. It is preferable that the amount of ascorbic acid-2-phosphate, measured 1 hour after the production of the skin external preparation, be 0-0.5% by mass, relative to the total mass of the skin external preparation.

<Betaine-Type Amphoteric Surfactant>

The skin external preparation according to the present invention further includes at least one betaine-type amphoteric surfactant selected from the group consisting of compounds represented by formula (1) or (2) shown below (hereinafter also referred to as "the specified betaine-type amphoteric surfactant").

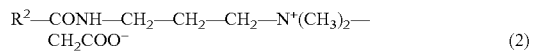

In formula (1), $R^1$ represents a linear or branched alkyl group of 6 to 30 carbon atoms. In formula (2), $R^2$ represents a linear or branched alkyl group of 8 to 30 carbon atoms.

The compound represented by general formula (1) (hereinafter also referred to as "compound (1)") has a betaine structure in which a linear or branched alkyl tertiary amine is bonded to acetic acid. Such a betaine structure imparts an excellent solubilization power and an excellent APPS stabilizing ability to the compound.

The compound represented by general formula (2) (hereinafter also referred to as "compound (2)") has a betaine structure in which a fatty acid, dimethylpropyldiamine and acetic acid are bonded together. Such a betaine structure also imparts an excellent solubilization power and an excellent APPS stabilizing ability to the compound.

By including a specific betaine structure (having a quaternary ammonium salt cation), the compounds (1) and (2) are soluble in water even in a pH range close to an isoelectric point, and it is thought that this is the reason the compounds exhibit excellent solubilization of APPS.

In the above general formula (1), $R^1$ represents a linear or branched alkyl group of 6 to 30 carbon atoms. It is preferable that $R^1$ be a linear or branched alkyl group of 10 to 30 carbon atoms, and more preferably a linear or branched alkyl group of 12 to 24 carbon atoms, from the viewpoints of raw material availability and the solubilization power of the surfactant. There are no particular limitations on the linear or branched alkyl group of 6 to 30 carbon atoms, and examples thereof include a lauryl group, myristyl group, cetyl group, stearyl group and isostearyl group.

There are no particular limitations on the specific compound used as the compound (1), and examples thereof include lauryl dimethylaminoacetate betaine, myristyl dimethylaminoacetate betaine, stearyl dimethylaminoacetate betaine, and coconut oil alkylaminoacetate betaine.

The compound (1) may be produced using conventional production methods, or commercially available products may be used. Examples of the commercially available products include the products Amphitol 24B and Amphitol 86B manufactured by Kao Corporation, the product Nikkol AM-301 manufactured by Nikko Chemicals Co., Ltd., the products Nissananon BF and Nissananon BL manufactured by NOF Corporation, and the products Rikabion A-100, Rikabion A-110, Rikabion A-200 and Rikabion A-700 manufactured by New Japan Chemicals Co., Ltd.

In the above general formula (2), $R^2$ represents a linear or branched alkyl group of 8 to 30 carbon atoms. It is preferable that $R^2$ be a linear or branched alkyl group of 10 to 30 carbon atoms, and more preferably a linear or branched alkyl group of 12 to 24 carbon atoms, from the viewpoints of raw material availability and the solubilization power of the surfactant. There are no particular limitations on the linear or branched alkyl group of 8 to 30 carbon atoms, and examples thereof include a lauryl group, myristyl group, cetyl group and stearyl group.

There are no particular limitations on the specific compound used as the compound (2), and examples thereof include lauramidopropyl dimethylaminoacetate betaine, myristamidopropyl dimethylaminoacetate betaine, coconut oil fatty acid amidopropyl dimethylaminoacetate betaine, palm kernel oil fatty acid amidopropyl dimethylaminoacetate betaine, and isostearamidopropyl dimethylaminoacetate betaine.

The compound (2) may be produced using conventional production methods, or commercially available products may be used. Examples of the commercially available products include the product Nikkol AM-3130N manufactured by Nikko Chemicals Co., Ltd., the products Softazoline CPB-R, Softazoline LPB-R and Softazoline PKPB manufactured by Kawaken Fine Chemicals Co., Ltd., and the products Obazoline BC, Obazoline LB, Obazoline LB-SF, Obazoline CAB-30 and Obazoline ISAB manufactured by Toho Chemical Industry Co., Ltd.

For the specified betaine-type amphoteric surfactant, a single compound may be used alone, or two or more compounds may be used in combination.

The amount of the specified betaine-type amphoteric surfactant, relative to the total mass of the skin external preparation, is preferably within a range from 0.1 to 10% by mass, and more preferably from 0.5 to 5% by mass. Provided the formulating amount is at least 0.1% by mass, the stability of the formulation is excellent, and the occurrence of precipitation or turbidity during storage is unlikely. If the amount exceeds 10% by mass, effects that correspond with the increased amount may not be obtained, with a possibility that the sensation upon using the formulation may deteriorate.

<Other Optional Components>

The skin external preparation of the present invention may further include at least one compound selected from among ascorbic acid, salts thereof, and ascorbic acid derivatives other than ascorbic acid-2-phosphate derivatives, unless inclusion of the compound impairs the effects of the present invention.

Examples of the salts include sodium salts and potassium salts.

Examples of ascorbic acid derivatives other than ascorbic acid-2-phosphate derivatives include ascorbic acid-3-phosphate-6-higher fatty acid esters and salts thereof, ascorbic acid-6-higher fatty acid esters and salts thereof, ascorbic acid-2,6-di-higher fatty acid esters and salts thereof, ascorbic acid-2,3,5,6-tetra-higher fatty acid esters and salts thereof, ascorbic acid-2-sulfate and salts thereof, and ascorbic acid-2-glucoside. Examples of the salts include sodium salts and potassium salts. Examples of the higher fatty acids include fatty acids of 8 to 22 carbon atoms.

Specific examples of the ascorbic acid derivatives include sodium ascorbic acid-3-phosphate-6-palmitate, ascorbyl 6-palmitate, ascorbyl 2,6-dipalmitate, ascorbyl 2,3,5,6-tetraisopalmitate, disodium ascorbic acid-2-sulfate, and ascorbic acid-2-glucoside.

In the skin external preparation, the phosphate group at position 2 of the APPS may undergo a rearrangement to position 3 over time. Accordingly, the skin external preparation of the present invention may include small amounts of sodium ascorbic acid-3-phosphate-6-palmitate over time, even though the compound is not formulated at the time of production. It is preferable that the amount of sodium ascorbic acid 3-phosphate-6-palmitate, measured 1 hour after the production of the skin external preparation, be 0-0.5% by mass, relative to the total mass of the skin external preparation.

The skin external preparation of the present invention may further include components typically used in skin preparations for external use, such as pharmaceutically acceptable carriers and additives for skin preparations for external use, unless the inclusion of the components impairs the effects of the present invention. Examples of the components include hydrocarbons, natural oils and fats, fatty acids, higher alcohols, alkyl glyceryl ethers, esters, silicone oils, polyhydric alcohols, monohydric lower alcohols, sugars, polymers, anionic surfactants, cationic surfactants, amphoteric surfactants that fall outside the definition for the specified betaine-type amphoteric surfactants, nonionic surfactants, natural surfactants, ultraviolet absorbers, powders, coloring materials, plant extracts, amino acids, peptides, vitamins, vitamin-like factors, preservatives, antioxidants, metal ion sequestering agents, moisturizing agents, anti-inflammatory agents, pH regulators, salts, organic acids, whitening agents, essential oils, terpenes, fragrances and water.

Specific examples of the above hydrocarbons include ozokerite, α-olefin oligomers, light isoparaffin, light liquid isoparaffin, squalene, squalane, synthetic squalane, phytosqualane, ceresin, paraffin, polyethylene powder, polybutene, microcrystalline wax, liquid isoparaffin, liquid paraffin, mineral oil and Vaseline.

Specific examples of the aforementioned natural oils and fats include natural waxes such as jojoba oil, carnauba wax, candelilla wax, rice bran wax, shellac, lanolin, mink sebaceous wax, spermaceti wax, sugarcane wax, sperm whale oil, beeswax, and montan wax, avocado oil, almond oil, olive oil, extra virgin olive oil, sesame seed oil, rice bran oil, rice oil, rice germ oil, corn oil, safflower oil, soybean oil, rape seed oil, persic oil, palm kernel oil, palm oil, castor oil, sunflower oil, high oleic sunflower oil, grape seed oil, cotton seed oil, coconut oil, hydrogenated coconut oil, beef tallow, hydrogenated oil, horse oil, mink oil, egg-yolk oil, egg-yolk fat oil, rose hip oil, kukui nut oil, evening primrose oil, wheat germ oil, peanut oil, *camellia* oil, *camellia kissi* seed oil, cacao butter, Japan wax, beef bone tallow, neatsfoot oil, swine tallow, equine tallow, ovine tallow, shea butter, macadamia nut oil and meadowfoam seed oil.

Specific examples of the aforementioned fatty acids include lauric acid, myristic acid, palmitic acid, stearic acid, behenic acid, oleic acid, linoleic acid, linolenic acid, γ-linolenic acid, isostearic acid, 12-hydroxystearic acid, undecylenic acid and coconut oil fatty acid.

Specific examples of the aforementioned higher alcohols include isostearyl alcohol, octyldodecanol, hexyldecanol, cholesterol, phytosterol, lauryl alcohol, myristyl alcohol, cetanol, stearyl alcohol, oleyl alcohol, behenyl alcohol and cetostearyl alcohol.

Specific examples of the aforementioned alkyl glyceryl ethers include batyl alcohol, chimyl alcohol, serachyl alcohol and isostearyl glyceryl ether.

Specific examples of the aforementioned esters include isopropyl myristate, butyl myristate, isopropyl palmitate, ethyl stearate, butyl stearate, ethyl oleate, ethyl linoleate, isopropyl linoleate, cetyl caprylate, hexyl laurate, isooctyl myristate, decyl myristate, myristyl myristate, cetyl myristate, octadecyl myristate, cetyl palmitate, stearyl stearate, decyl oleate, oleyl oleate, cetyl ricinoleate, isostearyl laurate, isotridecyl myristate, isocetyl myristate, isostearyl myristate, octyldodecyl myristate, 2-ethylhexyl palmitate, isocetyl palmitate, isostearyl palmitate, 2-ethylhexyl stearate, isocetyl stearate, isodecyl oleate, octyldodecyl oleate, octyldodecyl ricinoleate, ethyl isostearate, isopropyl isostearate, cetyl 2-ethylhexanoate, cetostearyl 2-ethylhexanoate, stearyl 2-ethylhexanoate, hexyl isostearate, ethylene glycol dioctanoate, ethylene glycol dioleate, propylene glycol dicaprylate, propylene glycol dicaprylate/dicaprate, propylene glycol dicaprate, propylene glycol dioleate, neopentyl glycol dicaprate, neopentyl glycol dioctanoate, glyceryl tricaprylate, glyceryl tri-2-ethylhexanoate, glyceryl tricaprylate/tricaprate, glyceryl tricaprylate/tricaprate/tristearate, glyceryl triundecylate, glyceryl triisopalmitate, glyceryl triisostearate, trimethylolpropane tri-2-ethylhexanoate, trimethylolpropane triisostearate, pentaerythrityl tetra-2-ethylhexanoate, pentaerythrityl tetramyristate, pentaerythrityl tetraisostearate, diglyceryl tetraisostearate, octyldodecyl neopentanoate, isocetyl octanoate, isostearyl octanoate, 2-ethylhexyl isopelargonate, hexyldecyl dimethyloctanoate, octyldodecyl dimethyloctanoate, 2-ethylhexyl isopalmitate, isocetyl isostearate, isostearyl isostearate, octyldodecyl isostearate, lauryl lactate, myristyl lactate, cetyl lactate, octyldodecyl lactate, triethyl citrate, acetyltriethyl citrate, acetyltributyl citrate, trioctyl citrate, triisocetyl citrate, trioctyldodecyl citrate, diisostearyl malate, 2-ethylhexyl hydroxystearate, di-2-ethylhexyl succinate, diisopropyl adipate, diisobutyl adipate, dioctyl adipate, diheptylundecyl adipate, diethyl sebacate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoylhydroxystearate, stearyl 12-stearoylhydroxystearate, isostearyl 12-stearoylhydroxystearate, polyoxyethylene (3) polyoxypropylene (1) cetyl ether acetate, polyoxyethylene (3) polyoxypropylene (1) isocetyl ether acetate, isononyl isononanoate, octyl isononanoate, tridecyl isononanoate, isotridecyl isononanoate and dicapryl carbonate.

Specific examples of the aforementioned silicone oils include methylpolysiloxane, methylphenylpolysiloxane, methylhydrogenpolysiloxane, methylcyclopolysiloxane, octamethylcyclotetrasiloxane, decamethylcyclopentasiloxane, dodecamethylcyclohexasiloxane, octamethyltrisiloxane, decamethyltetrasiloxane, tetradecamethylhexasiloxane, highly polymerized methylpolysiloxane, dimethylsiloxane-methyl(polyoxyethylene)siloxane-methyl(polyoxypropylene)siloxane copolymers, dimethylsiloxane-methyl(polyoxyethylene)siloxane copolymers, dimethylsiloxane-methyl(polyoxypropylene)siloxane copolymers, dimethylsiloxane-methylcetyloxysiloxane copolymers, dimethylsiloxane-methylstearoxysiloxane copolymers, polyether-modified silicone, alcohol-modified silicone, alkyl-modified silicone and amino-modified silicone.

Specific examples of the aforementioned polyhydric alcohols include ethylene glycol, diethylene glycol, triethylene glycol, polyethylene glycol, propylene glycol, dipropylene glycol, polypropylene glycol, glycerol, diglycerol, polyglycerol, 3-methyl-1,3-butanediol, 1,3-butanediol, 1,2-pentanediol, 1,2-hexanediol, 1,2-octanediol and neopentyl glycol.

Examples of the aforementioned monovalent lower alcohols include monovalent alcohols of 1 to 7 carbon atoms, and specific examples thereof include ethanol, isopropyl alcohol, 1-butanol, 2-butanol and benzyl alcohol.

Specific examples of the aforementioned sugars include mannitol, sorbitol, xylitol, maltitol, erythritol, pentaerythritol, glucose, sucrose, fructose, lactose, maltose, xylose and trehalose.

Specific examples of the aforementioned polymers include sodium alginate, carrageenan, agar, furcellaran, guar gum, polysaccharide (B-16 polymer) from *Alcaligenes latus* strain B-16, gellan gum, quince seed, konjac mannan, tamarind gum, tara gum, dextrin, starch, locust bean gum, gum arabic, gum gatti, karaya gum, gum tragacanth, arabinogalactan, pectin, quince, chitosan, curdlan, xanthan gum, cyclodextrin, dextran, pullulan, microcrystalline cellulose, methyl cellulose, ethyl cellulose, hydroxyethyl cellulose, hydroxypropyl cellulose, hydroxypropylmethyl cellulose, carboxymethyl cellulose, carboxy starch, cationized cellulose, starch phosphate ester, cationized guar gum, carboxymethyl-hydroxypropylated guar gum, hydroxypropylated guar gum, albumin, casein, gelatin, sodium polyacrylate, polyacrylic amide, carboxy vinyl polymers, polyethyleneimine, highly polymerized polyethylene glycol, polyvinyl alcohol, polyvinylpyrrolidone, polyvinyl ether, polyacrylamide, acrylic acid copolymers, methacrylic acid copolymers, maleic acid copolymers, vinylpyridine copolymers, ethylene-acrylic acid copolymers, vinylpyrrolidone-based polymers, vinyl alcohol-vinylpyrrolidone copolymers, nitrogen-substituted acrylamide-based polymers, amino-modified silicone, cationized polymers, dimethylacrylammonium-based polymers, acrylic acid-based anionic polymers, methacrylic acid-based anionic polymers, modified silicone, alkyl (C10 to C30) acrylate/methacrylate copolymers and polyoxyethylene/polyoxypropylene copolymers.

Specific examples of the aforementioned anionic surfactants include coconut oil fatty acid potassium, coconut oil fatty acid sodium, coconut oil fatty acid triethanolamine, potassium laurate, sodium laurate, triethanolamine laurate, potassium myristate, sodium myristate, isopropanolamine myristate, potassium palmitate, sodium palmitate, isopropanolamine palmitate, potassium stearate, sodium stearate, triethanolamine stearate, potassium oleate, sodium oleate, castor oil fatty acid sodium, zinc undecylenate, zinc laurate, zinc myristate, magnesium myristate, zinc palmitate, zinc stearate, calcium stearate, magnesium stearate, aluminum stearate, calcium myristate, magnesium myristate, aluminum dimyristate, aluminum isostearate, polyoxyethylene lauryl ether acetate, sodium polyoxyethylene lauryl ether acetate, polyoxyethylene tridecyl ether acetate, sodium polyoxyethylene tridecyl ether acetate, sodium stearoyl lactate, sodium isostearoyl lactate, sodium lauroyl sarcosine, coconut oil fatty acid sarcosine, sodium coconut oil fatty acid sarcosine, coconut oil fatty acid sarcosine triethanolamine, lauroyl sarcosine, potassium lauroyl sarcosine, lauroyl sarcosine triethanolamine, oleoyl sarcosine, sodium myristoyl sarcosine, sodium stearoyl glutamate, coconut oil fatty acid acylglutamic acid, potassium coconut oil fatty acid acylglutamate, sodium coconut oil fatty acid acylglutamate, coconut oil fatty acid acylglutamate triethanolamine, lauroyl acylglutamic acid, potassium lauroyl acylglutamate, sodium lauroyl acylglutamate, lauroyl acylglutamate triethanolamine, myristoyl acylglutamic acid, potassium myristoyl acylglutamate, sodium myristoyl acylglutamate, stearoyl acylglutamic acid, potassium stearoyl acylglutamate, disodium stearoyl acylglutamate, sodium hydrogenated beef tallow fatty acid acylglutamate, sodium coconut oil fatty acid/hydrogenated beef tallow fatty acid acylglutamate, sodium coconut oil fatty acid methylalanine, lauroyl methylalanine, sodium lauroyl methylalanine, lauroyl methylalanine triethanolamine, sodium myristoyl methylalanine, sodium lauroyl methyltaurine, potassium coconut oil fatty acid methyltaurine, sodium coconut oil fatty acid methyltaurine, magnesium coconut oil fatty acid methyltaurine, sodium myristoyl methyltaurine, sodium palmitoyl methyltaurine, sodium stearoyl methyltaurine, sodium oleoyl methyltaurine, sodium alkane sulfonate, sodium tetradecene sulfonate, dioctyl sodium sulfosuccinate, disodium lauryl sulfosuccinate, sodium coconut oil fatty acid ethyl ester sulfonate, sodium lauryl sulfate, triethanolamine lauryl sulfate, sodium cetyl sulfate, triethanolamine alkyl (11,13,15) sulfate, sodium alkyl (12,13) sulfate, triethanolamine alkyl (12,13) sulfate, ammonium alkyl (12,14,16) sulfate, diethanolamine alkyl (12 to 13) sulfate, triethanolamine alkyl (12 to 14) sulfate, triethanolamine alkyl (12 to 15) sulfate, magnesium-triethanolamine coconut oil alkyl sulfate, ammonium lauryl sulfate, potassium lauryl sulfate, magnesium lauryl sulfate, monoethanolamine lauryl sulfate, diethanolamine lauryl sulfate, sodium myristyl sulfate, sodium stearyl sulfate, sodium oleyl sulfate, triethanolamine oleyl sulfate, sodium polyoxyethylene lauryl ether sulfate, triethanolamine polyoxyethylene lauryl ether sulfate, sodium polyoxyethylene (1) alkyl (11,13,15) ether sulfate, triethanolamine polyoxyethylene (1) alkyl (11,13,15) ether sulfate, sodium polyoxyethylene (3) alkyl (11 to 15) ether sulfate, sodium polyoxyethylene (2) alkyl (12,13) ether sulfate, sodium polyoxyethylene (3) alkyl (12 to 14) ether sulfate, sodium polyoxyethylene (3) alkyl (12 to 15) ether sulfate, sodium polyoxyethylene (2) lauryl ether sulfate, sodium polyoxyethylene (3) myristyl ether sulfate, sodium higher fatty acid alkanolamide sulfate, lauryl phosphate, sodium lauryl phosphate, potassium cetyl phosphate, diethanolamine cetyl phosphate, polyoxyethylene oleyl ether phosphate, polyoxyethylene lauryl ether phosphate, sodium polyoxyethylene lauryl ether phosphate, polyoxyethylene cetyl ether phosphate, sodium polyoxyethylene cetyl ether phosphate, polyoxyethylene stearyl ether phosphate, polyoxyethylene oleyl ether phosphate, sodium polyoxyethylene oleyl ether phosphate, polyoxyethylene alkyl phenyl ether phosphate, sodium polyoxyethylene alkyl phenyl ether phosphate, triethanolamine polyoxyethylene alkyl phenyl ether phosphate, polyoxyethylene octyl ether phosphate, polyoxyethylene (10) alkyl (12,13) ether phosphate, polyoxyethylene alkyl (12 to 15) ether phosphate, polyoxyethylene alkyl (12 to 16) ether phosphate, triethanolamine polyoxyethylene lauryl ether phosphate and diethanolamine polyoxyethylene oleyl ether phosphate.

Specific examples of the aforementioned cationic surfactants include dioctylamine, dimethylstearylamine, trilaurylamine, diethylaminoethylamide stearate, lauryl trimethylammonium chloride, cetyl trimethylammonium chloride, cetyl trimethylammonium bromide, cetyl trimethylammonium saccharin, stearyl trimethylammonium chloride, alkyl (20 to 22) trimethylammonium chloride, lauryl trimethylammonium bromide, alkyl (16,18) trimethylammonium chloride, stearyl trimethylammonium bromide, stearyl trimethylammonium saccharin, alkyl (28) trimethylammonium chloride, di(polyoxyethylene) oleyl methylammonium (2EO) chloride, dipolyoxyethylene stearyl methylammonium chloride, polyoxyethylene (1) polyoxypropylene (25) diethylmethyl ammonium chloride, tri(polyoxyethylene)stearyl ammonium (5EO) chloride, distearyl dimethylammonium chloride, dialkyl (12 to 15) dimethylammonium chloride, dialkyl (12 to 18) dimethylammonium chloride, dialkyl (14 to 18) dimethylammonium chloride, dicocoyl dimethylammonium chloride, dicetyl dimethylammonium chloride, isostearyl lauryl dimethylammonium chloride, benzalkonium chloride, myristyl dimethyl benzyl ammonium chloride, lauryl dimethyl(ethylbenzyl)ammonium chloride, stearyl dimethyl benzyl ammonium chloride, lauryl pyridinium chloride, cetyl pyridinium chloride, lauroyl cholamino formylmethyl pyridinium chloride, stearoyl cholamino formylmethylpyridinium chloride, alkyl isoquinolinium bromide, methyl benzethonium chloride and benzethonium chloride.

In the above list of surfactants, the number preceding "EO" refers to the average polymerization degree of oxyethylene in the polyoxyethylene unit.

Specific examples of the aforementioned amphoteric surfactants that fall outside the definition for the specified betaine-type amphoteric surfactants include 2-alkyl-N-carboxymethyl-N-hydroxyethyl imidazolium betaine, alkyl diaminoethyl glycine hydrochloride, sodium lauryl diaminoethyl glycine, sodium undecyl hydroxyethyl imidazolium betaine, undecyl-N-carboxymethyl imidazolium betaine, disodium coconut oil fatty acid acyl-N-carboxyethyl-N-hydroxyethyl ethylenediamine, disodium coconut oil fatty acid acyl-N-carboxyethoxyethyl-N-carboxyethyl ethylenediamine, disodium coconut oil fatty acid acyl-N-carboxymethoxyethyl-N-carboxymethyl ethylenediamine, sodium laurylaminopropionate, sodium laurylaminodipropionate, triethanolamine laurylaminopropionate, sodium palm oil fatty acid acyl-N-carboxyethyl-N-hydroxyethyl ethylenediamine, stearyl dihydroxyethyl betaine and lauryl hydroxysulfobetaine.

Specific examples of the aforementioned nonionic surfactants include polyoxyethylene (10) alkyl (12,13) ether, polyoxyethylene lauryl ether, polyoxyethylene cetyl ether, polyoxyethylene stearyl ether, polyoxyethylene oleyl ether, polyoxyethylene (3,7,12) alkyl (12 to 14) ether, polyoxyethylene tridecyl ether, polyoxyethylene myristyl ether, polyoxyethylene sec-alkyl (14) ether, polyoxyethylene isocetyl ether, polyoxyethylene cetostearyl ether, polyoxyethylene (2,10,20) isostearyl ether, polyoxyethylene oleylcetyl ether, polyoxyethylene (20) alkyl ether, polyoxyethylene octyldodecyl ether, polyoxyethylene behenyl ether, polyoxyethylene octylphenyl ether, polyoxyethylene nonylphenyl ether, polyoxyethylene dinonylphenyl ether, polyoxyethylene (2) polyoxypropylene (2) decyl ether, polyoxyethylene (4) polyoxypropylene (2) decyl ether, polyoxyethylene (7) polyoxypropylene (2) decyl ether, polyoxyethylene (8) polyoxypropylene (2) decyl ether, polyoxyethylene (10) polyoxypropylene (2) decyl ether, polyoxyethylene (15) polyoxypropylene (2) decyl ether, polyoxyethylene (20) polyoxypropylene (2) decyl ether, polyoxyethylene (30) polyoxypropylene (2) decyl ether, polyoxyethylene (40) polyoxypropylene (2) decyl ether, polyoxyethylene (8) polyoxypropylene (2) lauryl ether, polyoxyethylene (15) polyoxypropylene (4) lauryl ether, polyoxyethylene (10) polyoxypropylene (4) cetyl ether, polyoxyethylene (20) polyoxypropylene (4) cetyl ether, polyoxyethylene (20) polyoxypropylene (8) cetyl ether, polyoxyethylene (20) polyoxypropylene (6) decyltetradecyl ether, polyoxyethylene (30) polyoxypropylene (6) decyltetradecyl ether, polyoxyethylene (5) polyoxypropylene (5) glycol, polyoxyethylene (5) polyoxypropylene (30) glycol, polyoxyethylene (10) polyoxypropylene (8) glycol, polyoxyethylene (16) polyoxypropylene (17) glycol, polyoxyethylene (20) polyoxypropylene (20) glycol, polyoxyethylene (25) polyoxypropylene (30) glycol, polyoxyethylene (35) polyoxypropylene (40) glycol, polyoxyethylene (100) polyoxypropylene (40) glycol, polyoxyethylene (300) polyoxypropylene (55) glycol, polyoxyethylene (400) polyoxypropylene (70) glycol, polyoxyethylene (1) polyoxypropylene (1,2,4,8) cetyl ether, polyoxyethylene (5) polyoxypropylene (1) cetyl ether, polyoxyethylene (10) polyoxypropylene (1) cetyl ether, polyoxyethylene (20) polyoxypropylene (1) cetyl ether, polyethylene glycol monolaurate, ethylene glycol monostearate, polyethylene glycol monostearate, polyethylene glycol monooleate, ethylene glycol fatty acid ester, self-emulsifying ethylene glycol monostearate, diethylene glycol laurate, polyethylene glycol myristate, polyethylene glycol palmitate, diethylene glycol stearate, self-emulsifying polyethylene glycol (2) monostearate, polyethylene glycol isostearate, ethylene glycol dioctanoate, diethylene glycol dilaurate, polyethylene glycol dilaurate, polyethylene glycol (150) dipalmitate, ethylene glycol distearate, diethylene glycol distearate, polyethylene glycol distearate, ethylene glycol dioleate, polyethylene glycol dioleate, polyethylene glycol diricinoleate, polyoxyethylene (20) sorbitan monolaurate, polyoxyethylene (20) sorbitan monopalmitate, polyoxyethylene (6) sorbitan monostearate, polyoxyethylene (20) sorbitan monostearate, polyoxyethylene (20) sorbitan tristearate, polyoxyethylene (6) sorbitan monooleate, polyoxyethylene (20) sorbitan monooleate, polyoxyethylene (20) sorbitan trioleate, polyoxyethylene (20) coconut oil fatty acid sorbitan, polyoxyethylene (10 to 80) sorbitan monolaurate, polyoxyethylene sorbitan tristearate, polyoxyethylene (20) sorbitan isostearate, polyoxyethylene (150) sorbitan tristearate, polyoxyethylene sorbitol monolaurate, polyoxyethylene (40) sorbitol oleate, polyoxyethylene (4) sorbitol tetraoleate, polyoxyethylene (3) sorbitol tristearate, polyoxyethylene (30) sorbitol tetraoleate, polyoxyethylene (40) sorbitol tetraoleate, polyoxyethylene (60) sorbitol tetraoleate, polyoxyethylene (3) sorbitol isostearate, polyoxyethylene (60) sorbitol tetrasteate, polyoxyethylene (6) sorbitol hexaoleate, polyoxyethylene sorbitol hexastearate, polyoxyethylene (40) sorbitol pentaoleate, polyoxyethylene (3) glyceryl triisostearate, polyoxyethylene (5) glyceryl triisostearate, polyoxyethylene (10) glyceryl triisostearate, polyoxyethylene (20) glyceryl triisostearate, polyoxyethylene (30) glyceryl triisostearate, polyoxyethylene (40) glyceryl triisostearate, polyoxyethylene (50) glyceryl triisostearate, polyoxyethylene (60) glyceryl triisostearate, polyoxyethylene (3) glyceryl isostearate, polyoxyethylene (5) glyceryl isostearate, polyoxyethylene (6) glyceryl isostearate, polyoxyethylene (8) glyceryl isostearate, polyoxyethylene (10) glyceryl isostearate, polyoxyethylene (15) glyceryl isostearate, polyoxyethylene (20) glyceryl isostearate, polyoxyethylene (25) glyceryl isostearate, polyoxyethylene (30) glyceryl isostearate, polyoxyethylene (40) glyceryl isostearate, polyoxyethylene (50) glyceryl isostearate, polyoxyethylene (60) glyceryl isostearate, polyoxyethylene (3) glyceryl tristearate, polyoxyethylene (4) glyceryl tristearate, polyoxyethylene (5) glyceryl tristearate, polyoxyethylene (6) glyceryl tristearate, polyoxyethylene (10) glyceryl tristearate, polyoxyethylene (20) glyceryl tristearate, polyoxyethylene (4) glyceryl distearate, polyoxyethylene (3) glyceryl trioleate, polyoxyethylene (5) glyceryl trioleate, polyoxyethylene (10) glyceryl trioleate, polyoxyethylene (20) glyceryl trioleate, polyoxyethylene (30) glyceryl trioleate, polyoxyethylene (40) glyceryl trioleate, polyoxyethylene (50) glyceryl trioleate, polyoxyethylene (60) glyceryl trioleate, polyoxyethylene castor oil, polyoxyethylene hydrogenated castor oil, polyoxyethylene (10) hydrogenated castor oil, polyoxyethylene (20) hydrogenated castor oil, polyoxyethylene (40) hydrogenated castor oil, polyoxyethylene (50) hydrogenated castor oil, polyoxyethylene (60) hydrogenated castor oil, lipophilic glycerol monostearate, lipophilic glycerol monooleate, self-emulsifying glycerol monostearate, coconut oil fatty acid glyceryl, glycerol laurate, glyceryl myristate, glyceryl isostearate, glyceryl ricinoleate, glyceryl monohydroxystearate, glycerol oleate, glyceryl linoleate, glyceryl erucate, glyceryl behenate, wheat germ oil fatty acid glyceride, safflower oil fatty acid glyceryl, hydrogenated soybean fatty acid glyceryl, saturated fatty acid glyceride, cotton seed oil fatty acid glyceryl, glyceryl monoisostearate monomyristate, beef tallow monoglyceride, monolanolin fatty acid glyceryl, glyceryl sesquioleate, glyceryl distearate, glyceryl diisostearate, glyceryl diarachidate, sorbitan monolaurate, sorbitan monopalmitate, sorbitan monostearate, sorbitan monoisostearate, sorbitan monooleate, sorbitan sesquistearate, sorbitan sesquioleate, sorbitan tristearate, sorbitan trioleate, coconut oil fatty acid sorbitan, sorbitan isostearate, sorbitan sesquiisostearate, sorbitan distearate, diglyceryl isopalmitate, tetraglyceryl monolaurate, hexaglyceryl monolaurate, decaglyceryl monolaurate, decaglyceryl monomyristate, diglyceryl monostearate, tetraglyceryl monostearate, hexaglyceryl monostearate, decaglyceryl monostearate, diglyceryl monoisostearate, tetraglyceryl monoisostearate, hexaglyceryl monoisostearate, decaglyceryl monoisostearate, diglyceryl monooleate, tetraglyceryl monooleate, hexaglyceryl monooleate, decaglyceryl monooleate, diglyceryl sesquioleate, tetraglyceryl diisostearate, hexaglyceryl diisostearate, decaglyceryl diisostearate, hexaglyceryl distearate, decaglyceryl distearate, diglyceryl triisostearate, decaglyceryl tristearate, decaglyceryl trioleate, diglyceryl tetraisostearate, decaglyceryl pentastearate, hexaglyceryl pentaoleate, decaglyceryl pentaoleate, decaglyceryl heptastearate, decaglyceryl decastearate, decaglyceryl decaoleate, hexaglyceryl condensed ricinoleate, sucrose fatty acid ester, coconut oil fatty acid sucrose ester, alkyl glucoside, coconut oil alkyl dimethylamine oxide, lauryl dimethylamine oxide, dihydroxyethyl lauryl dimethylamine oxide, stearyl dimethylamine oxide, oleyl dimethylamine oxide, polyoxyethylene coconut oil alkyl dimethylamine oxide, dextrin palmitate, dextrin stearate and dextrin myristate.

In the above list of nonionic surfactants, the number in parentheses following polyoxyethylene or polyoxypropylene refers to the average polymerization degree of oxyethylene in the polyoxyethylene unit or the average polymerization degree of oxypropylene in the polyoxypropylene unit respectively.

Specific examples of the aforementioned natural surfactants include saponin, lecithin, hydrogenated lecithin, soybean phospholipid, hydrogenated soybean phospholipid, soybean lysophospholipid, hydrogenated soybean lysophospholipid, egg-yolk lecithin, hydrogenated egg-yolk lysophosphatidylcholine, phosphatidylcholine, phosphatidylethanolamine, phosphatidylserine, sphingophospholipid, sphingomyelin, ganglioside, bile acid, cholic acid, deoxycholic acid, sodium cholate, sodium deoxycholate, spiculisporic acid, rhamnolipid, trehalose lipid, sophorolipid, mannosyl erythritol lipid and sodium surfactin.

Specific examples of the aforementioned ultraviolet absorbers include para-aminobenzoic acid and para-aminobenzoic acid derivatives such as ethyl para-aminobenzoate, glyceryl para-aminobenzoate, amyl para-dimethylaminobenzoate and 2-ethylhexyl para-dimethylaminobenzoate, cinnamic acid derivatives such as benzyl cinnamate, glyceryl mono-2-ethyl hexanoate di-para-methoxycinnamate, methyl 2,4-diisopropylcinnamate, ethyl 2,4-diisopropylcinnamate, potassium para-methoxycinnamate, sodium para-methoxycinnamate, isopropyl para-methoxycinnamate, 2-ethylhexyl para-methoxycinnamate, 2-ethoxyethyl para-methoxycinnamate and ethyl para-ethoxycinnamate, urocanic acid and urocanic acid derivatives such as ethyl urocanate, benzophenone derivatives such as 2,4-dihydroxybenzophenone, 2,2',4,4'-tetrahydroxybenzophenone, sodium 2-hydroxy-4-methoxy-5-sulfobenzophenone, 2-hydroxy-4-methoxybenzophenone-5-sulfonate, 2-hydroxy-4-methoxybenzophenone, 2,2'-dihydroxy-4,4'-dimethoxybenzophenone and sodium 2,2'-dihydroxy-4,4'-dimethoxy-5-sulfobenzophenone, salicylic acid derivatives such as ethylene glycol salicylate, 2-ethylhexyl salicylate, phenyl salicylate, benzyl salicylate, p-tert-butylphenyl salicylate, homomethyl salicylate and 3,3,5-trimethylcyclohexyl salicylate, as well as 2-(2'-hydroxy-5'-methoxyphenyl)benzotriazole and 4-tert-butyl-4'-methoxybenzoyl methane.

Specific examples of the aforementioned powders and coloring materials include kaolin, silicic anhydride, magnesium aluminum silicate, synthetic sodium magnesium silicate, sericite, talc, boron nitride, mica, montmorillonite, hemp cellulose powder, wheat starch, silk powder, maize starch; natural dyes such as nitro dyes, azo dyes, nitroso dyes, triphenylmethane dyes, xanthene dyes, quinoline dyes, anthraquinone dyes, indigo dyes, pyrene dyes, phthalocyanine dyes, flavonoids, quinones, porphyrins, water-soluble annatto, squid ink powder, caramel, guaiazulene, gardenia blue, gardenia yellow, cochineal, shikonin, sodium copper chlorophyllin, paprika dye, safflower red, safflower yellow, laccaic acid and riboflavin butyrate ester; as well as carbon black, yellow iron oxide, black iron oxide, red iron oxide, iron blue, ultramarine blue, zinc oxide, chromium oxide, titanium oxide, black titanium oxide, zirconium oxide, chromium hydroxide, alumina, magnesium oxide, barium sulfate, aluminum hydroxide, calcium carbonate, lithium cobalt titanate, manganese violet and pearl pigments.

Specific examples of the aforementioned plant extracts include *Angelica keiskei* extract, *Uncaria gambir* extract, avocado extract, sweet hydrangea leaf extract, *Gynostemma pentaphyllum* extract, *Althaea officinalis* extract, *Arnica montana* extract, oil-soluble *Arnica montana* extract, almond extract, aloe extract, *styrax* benzoin extract, *Ginkgo biloba* extract, stinging nettle extract, iris root extract, fennel extract, turmeric extract, dog rose fruit extract, *Echinacea* leaf extract, *Scutellaria* root extract, *Phellodendron* bark extract, *Coptis japonica* extract, barley extract, okra extract, *Hypericum erectum* extract, oil-soluble *Hypericum erectum* extract, *Lamium album* extract, oil-soluble *Lamium album* extract, *Ononis spinosa* extract, *Nasturtium officinale* extract, orange extract, orange flower water, seaweed extract, persimmon tannin, *pueraria* root extract, Japanese valerian extract, cattail extract, chamomile extract, oil-soluble chamomile extract, chamomile water, wild oat extract, carrot extract, oil-soluble carrot extract, carrot oil, *Artemisia capillaris* extract, licorice extract, powdered licorice extract, licorice flavonoid, *cantharides* tincture, raspberry extract, kiwifruit extract, cinchona extract, cucumber extract, apricot kernel extract, quince seed extract, *Gardenia Florida* extract, *Sasa albomarginata* extract, *Sophora augustifolia* extract, walnut shell extract, grapefruit extract, *clematis* extract, black sugar extract, *chlorella* extract, mulberry bark extract, cinnamon bark extract, gentian extract, geranium herb extract, black tea extract, *Nuphar japonica* extract, burdock root extract, oil-soluble burdock root extract, wheat germ extract, hydrolyzed wheat powder, rice bran extract, fermented rice bran extract, comfrey extract, asiasarum root extract, saffron extract, *Saponaria officinalis* extract, oil-soluble *salvia* extract, *Crataegus cuneata* extract, *Zanthoxylum piperitum* extract, shiitake mushroom extract, powdered shiitake mushroom extract, *rehmannia* root extract, *lithospermum* root extract, oil-soluble *lithospermum* root extract, *Perilla* herb extract, linden extract, oil-soluble linden extract, *Filipendula* extract, peony root extract, *Coix lacryma-jobi* extract, ginger extract, oil-soluble ginger extract, ginger tincture, *calamus* root extract, white birch extract, oil-soluble white birch extract, white birch sap, *Lonicera japonica* extract, *Equisetum arvense* extract, oil-soluble *Equisetum arvense* extract, scordinin, *stevia* extract, ivy extract, whitethorn extract, *Sambucus nigra* extract, *Juniperus communis* extract, *Achillea millefolium* extract, oil-soluble *Achillea millefolium* extract, peppermint extract, sage extract, oil-soluble sage extract, sage water, mallow extract, celery extract, *Cnidium officinale* extract, *Cnidium officinale* water, *swertia* herb extract, soybean extract, jujube extract, thyme extract, green tea extract, dried and distilled tea leaf solution, tea seed extract, clove extract, *citrus unshiu* peel extract, *Camellia japonica* extract, *Centella asiatica* extract, oil-soluble *Juglans regia* extract, *Lansium domesticum* extract, *Terminalia* extract, chili pepper tincture, *Angelica acutiloba* extract, oil-soluble *Angelica acutiloba* extract, *Angelica acutiloba* water, *Calendula officinalis* extract, oil-soluble *Calendula officinalis* extract, soy milk powder, peach kernel extract, bitter orange peel extract, *Houttuynia cordata* extract, tomato extract, *Potentilla tormentilla* Schrk extract, fermented soybean extract, ginseng extract, oil-soluble ginseng extract, garlic extract, wild rose extract, oil-soluble wild rose extract, malt extract, malt root extract, ophiopogon tuber extract, parsley extract, rye leaf juice concentrate, peppermint distillate, witch hazel water, witch hazel extract, rose extract, *parietaria* extract, *Isodon japonicus* extract, *Eriobotrya japonica* leaf extract, oil-soluble *Eriobotrya japonica* leaf extract, butcher's broom extract, powdered butcher's broom extract, grape extract, grape leaf extract, grape water, hayflower extract, *Luffa cylindrica* extract, *Luffa cylindrica* water, safflower extract, oil-soluble *Tilia miqueliana* extract, *Tilia miqueliana* water, *Paeonia suffruticosa* extract, hops extract, oil-soluble hops extract, pine extract, milk thistle extract, horse chestnut extract, oil-soluble horse chestnut extract, *Sapindus mukurossi* extract, *Melissa officinalis* extract, *melilot* extract, peach leaf extract, oil-soluble peach leaf extract, bean sprout extract, *Centaurea cyanus* flower extract, *Centaurea cyanus* flower distillate, *eucalyptus* extract, saxifrage extract, lily extract, *coix* seed extract, oil-soluble *coix* seed extract, *Artemisia princeps* extract, *Artemisia princeps* water, lavender extract, lavender water, apple extract, *Gaenoderma lucidum* extract, lettuce extract, lemon extract, *Astragalus sinicus* extract, rose water, rosemary extract, oil-soluble rosemary extract, *Anthemis nobilis* extract and *Sanguisorba officinalis* extract.

Specific examples of the aforementioned amino acids and peptides include glycine, alanine, valine, leucine, isoleucine, serine, threonine, phenylalanine, tyrosine, tryptophan, cystine, cysteine, methionine, proline, hydroxyproline, aspartic acid, asparagine, glutamic acid, glutamine, arginine, histidine, lysine, γ-aminobutyric acid, DL-pyrrolidonecarboxylic acid, ε-aminocaproic acid, hydrolyzed elastin, water-soluble elastin, hydrolyzed collagen, water-soluble collagen, casein, glutathione, wheat peptide and soybean peptide.

Specific examples of the aforementioned vitamins and vitamin-like factors include vitamin A compounds such as retinol, retinal, retinoic acid, retinol acetate and retinol palmitate, carotenoids such as α-carotene, β-carotene, γ-carotene, δ-carotene, lycopene, zeaxanthin, cryptoxanthin, echinenon and astaxanthin, vitamin $B_1$ compounds such as thiamines, vitamin $B_2$ compounds such as riboflavins, vitamin $B_6$ compounds such as pyridoxine, pyridoxal and pyridoxamine, vitamin $B_{12}$ compounds such as cyanocobalamin, folic acids, nicotinic acid, nicotinamide, pantothenic acids, biotins, vitamin D compounds such as ergocalciferol and cholecalciferol, vitamin E compounds such as d-α-tocopherol, DL-α-tocopherol, dl-α-tocopherol acetate, dl-α-tocopherol succinate, β-tocopherol, γ-tocopherol and d-δ-tocopherol, ubiquinones, vitamin K compounds, carnitine, ferulic acid, γ-oryzanol, α-lipoic acid and orotic acid.

Specific examples of the aforementioned preservatives include benzoic acid, sodium benzoate, undecylenic acid, salicylic acid, sorbic acid, potassium sorbate, dehydroacetic acid, sodium dehydroacetate, isobutyl para-hydroxybenzoate, isopropyl para-hydroxybenzoate, ethyl para-hydroxybenzoate, butyl para-hydroxybenzoate, propyl para-hydroxybenzoate, benzyl para-hydroxybenzoate, methyl para-hydroxybenzoate, sodium methyl para-hydroxybenzoate, phenoxyethanol, light-sensitive dye No. 101, light-sensitive dye No. 201 and light-sensitive dye No. 401.

Specific examples of the aforementioned antioxidants include butylhydroxyanisole, butylhydroxytoluene, propyl gallate, erythorbic acid, sodium erythorbate, para-hydroxyanisole and octyl gallate.

Specific examples of the aforementioned metal ion sequestering agents include trisodium ethylenediamine hydroxyethyl triacetate, edetic acid, disodium edetate, trisodium edetate, tetrasodium edetate, sodium citrate, gluconic acid, phytic acid, sodium polyphosphate, sodium metaphosphate and tetrasodium hydroxyethane diphosphonate.

Specific examples of the aforementioned moisturizing agents include hyaluronic acid, sodium hyaluronate, sodium chondroitin sulfate, sodium lactate, sodium pyrrolidone carboxylate, betaine, cultured lactic acid bacteria solution, yeast extract and ceramide.

Specific examples of the aforementioned anti-inflammatory agents include glycyrrhizic acid, trisodium glycyrrhizinate, dipotassium glycyrrhizinate, monoammonium glycyrrhizinate, β-glycyrrhetinic acid, glycerol glycyrrhetinate, stearyl glycyrrhetinate, lysozyme chloride, hydrocortisone and allantoin.

Specific examples of the aforementioned pH regulators include sodium hydroxide, potassium hydroxide and triethanolamine.

Specific examples of the aforementioned salts include sodium chloride, potassium chloride, magnesium chloride, sodium sulfate, magnesium sulfate, sodium tartarate, sodium malate, sodium glutamate and sodium aspartate.

Specific examples of the aforementioned organic acids include citric acid, glycolic acid, tartaric acid, lactic acid and malic acid.

Specific examples of the aforementioned whitening agents include arbutin, α-arbutin and placenta extract.

Specific examples of the aforementioned essential oils include *angelica* oil, ylang ylang oil, elemi oil, orange oil, chamomile oil, Roman chamomile oil, cardamon oil, *calamus* oil, galbanum oil, camphor oil, carrot seed oil, clary sage oil, grapefruit oil, clove oil, cinnamon bark oil, coriander oil, cypress oil, sandalwood oil, cedarwood oil, citronella oil, cinnamon leaf oil, jasmine absolute, juniper berry oil, ginger extract, spearmint oil, sage oil, cedar oil, geranium oil, thyme oil, tea tree oil, nutmeg oil, niaouli oil, *Citrus neroli* oil, pine oil, basil oil, mentha oil, patchouli oil, palmarosa oil, fennel oil, petitgrain oil, black pepper oil, frankincense oil, vetiver oil, peppermint oil, bergamot oil, benzoin oil, bois de rose oil, marjoram oil, mandarin oil, myrrh oil, *melissa* oil, *eucalyptus* oil, yuzu oil, lime oil, ravensara oil, lavandin oil, lavender oil, linden oil, lemon oil, lemon grass oil, rose oil, rosewood oil, rosemary oil and lovage oil.

Specific examples of the aforementioned terpenes include limonene, pinene, terpinene, terpinolene, myrcene and longifolene.

Any one of the above components may be used alone, or two or more components may be used in combination.

Among the above-mentioned components, it is preferable that at least one surfactant selected from the group consisting of the anionic surfactants, the cationic surfactants, the amphoteric surfactants that fall outside the definition for the specified betaine-type amphoteric surfactants, and the nonionic surfactants be formulated in the skin external preparation.

In those cases where the skin external preparation according to the present invention is a cosmetic material, other known cosmetic raw materials may also be formulated to the skin preparation in typical concentrations. For example, any of the cosmetic raw materials disclosed in "Keshouhin genryou kijun" (Standards of raw materials of cosmetics), second edition, notes, edited by the Society of Japanese Pharmacopoeia, 1984 (published by Yakuji Nippo Ltd.), "Keshouhin genryou kijun-gai seibun kikaku" (Standards of raw materials of cosmetics, nonstandard ingredients), edited under the supervision of the Pharmaceutical Affairs Bureau Evaluation and Registration Division of the Ministry of Health and Welfare, 1993 (published by Yakuji Nippo Ltd.), "Keshouhin genryou kijun-gai seibun kikaku tsuiho" (Standards of raw materials of cosmetics, nonstandard ingredients supplement), edited under the supervision of the Pharmaceutical Affairs Bureau Evaluation and Registration Division of the Ministry of Health and Welfare, 1993 (published by Yakuji Nippo Ltd.), "Keshouhin shubetsu kyoka kijun" (Standards of cosmetic classification permission), edited under the supervision of the Pharmaceutical Affairs Bureau Evaluation and Registration Division of the Ministry of Health and Welfare, 1993 (published by Yakuji Nippo Ltd.), "Keshouhin shubetsu haigou seibun kikaku" (Standards of cosmetic classification ingredients), edited under the supervision of the Pharmaceutical Affairs Bureau Evaluation and Registration Division of the Ministry of Health and Welfare, 1997 (published by Yakuji Nippo Ltd.), or "Keshouhin genryou jiten" (Dictionary of cosmetics raw materials), 1991 (published by Nikko Chemicals Co., Ltd.) may be used.

There are no particular limitations on the form of the skin external preparation of the present invention, and any form that enables the preparation to be brought into contact with the skin at the time of use may be selected as appropriate in accordance with the intended application. For example, a lotion, milky lotion, cream or pack may be used.

The skin external preparation of the present invention is particularly effective in lotion-type formulations where precipitates tend to be very noticeable.

The pH of the skin external preparation of the present invention is preferably within a range from 6.5 to 7.5. Provided the pH satisfies this range, the stability of the APPS is favorable, and the stability of the preparation further improves.

The pH refers to the value at 25° C., and can be measured using a pH meter.

The skin external preparation of the present invention can be produced by formulating: the APPS; at least one of the specific betaine-type amphoteric surfactants; and the above-mentioned optional components. At this time, no ascorbic acid-2-phosphate derivatives besides APPS are formulated.

The formulation process can be conducted by normal methods in accordance with the desired form of the preparation.

In the present invention, by including APPS and the specific betaine-type amphoteric surfactant, and excluding any ascorbic acid-2-phosphate derivatives besides the APPS, the occurrence of precipitation or turbidity within the skin external preparation over time can be suppressed.

As a result, the skin external preparation of the present invention can be used favorably within all manner of skin preparations for external use, including cosmetic materials and pharmaceutical preparations, and is particularly useful in cosmetic materials.

Although the reasons for the suppression of the occurrence of precipitation or turbidity over time are not entirely clear, they are thought to include the following. Namely, in skin preparations for external use containing APPS, decomposition of the APPS tends to result in the generation of a precipitate of sodium palmitate which is insoluble in water, but in the present invention, it is thought that by adding the specific betaine-type amphoteric surfactant, the sodium palmitate precipitate generated by decomposition can be solubilized. Further, it is also thought that by adding the specific betaine-type amphoteric surfactant to the skin external preparation containing APPS, some type of interaction occurs between the surfactant and the APPS that suppresses the decomposition of APPS and the generation of precipitates, thereby improving the formulation stability.

EXAMPLES

The present invention is described below in further detail using a series of examples, but the present invention is in no way limited by these examples.

Examples 1 to 11, Comparative Examples 1 to 8

Components shown in Table 1 or 2 (units: % by mass) were dispersed or dissolved uniformly by stirring to form a series of lotions.

Each of the obtained lotions was subjected to the evaluations described below. The results are shown in Tables 1 and 2.

[1. Evaluation of Precipitation]

For each of the obtained lotions, the occurrence of precipitates in the lotion was evaluated visually, immediately after preparation of the lotion and then again following storage for one month at 40° C. (following standing for one month in a 40° C. constant temperature bath), and the level of precipitation was evaluated against the following criteria.

A: no precipitation was observed
B: minor precipitation was observed
C: significant precipitation was observed

[2. Evaluation of Storage Stability]

The APPS retention rate (%) following storage of each of the obtained lotions for one month at 40° C. (following standing for one month in a 40° C. constant temperature bath) was calculated using the formula (3) shown below, and the storage stability was evaluated on the basis of the retention rate. A higher retention rate indicates superior storage stability. The retention rate is preferably 90% or higher.

Retention rate (%)=100×[APPS concentration within lotion after storage for one month at 40° C. (%)/ APPS concentration within lotion immediately after preparation (%)]  (3)

The APPS concentration was measured by high-performance liquid chromatography under the measurement conditions listed below.

(High-Performance Liquid Chromatography Measurement Conditions)

Column: Shodex C18P 4E (product name), manufactured by Showa Denko K.K.
Column temperature: 40° C.
Eluent: 0.03 M aqueous solution of potassium dihydrogen phosphate/acetonitrile=4/6 (volumetric ratio)
Flow rate: 0.7 mL/minute
Detection: UV 265 nm

TABLE 1

| | | Example | | | Comparative Example | | |
|---|---|---|---|---|---|---|---|
| | | 1 | 2 | 3 | 1 | 2 | 3 |
| Composition (% by mass) | APPS | 1 | 1 | 1 | 1 | 1 | 1 |
| | glycerol | 4 | 4 | 4 | 4 | 4 | 4 |
| | 1,3-butylene glycol | 4 | 4 | 4 | 4 | 4 | 4 |
| | lauryl dimethylaminoacetate betaine 26% aqueous solution | 3.3 | | | | | |
| | coconut oil fatty acid amidopropyl dimethylaminoacetate betaine 30% aqueous solution | | 3.8 | | | | |
| | isostearamidopropyl dimethylaminoacetate betaine 31% aqueous solution | | | 3.2 | | | |
| | decaglyceryl monostearate | | | | 1 | | |
| | polyoxyethylene (15) glyceryl monostearate | | | | | 1 | |
| | polyoxyethylene (20) sorbitan monooleate | | | | | | |
| | polyoxyethylene (30) sorbitol tetraoleate | | | | | | |
| | sodium polyoxyethylene (3) lauryl ether sulfate 25% aqueous solution | | | | | | |
| | cetyl trimethylammonium chloride 30% aqueous solution | | | | | | |
| | sodium laurylaminodipropionate 30% aqueous solution | | | | | | |
| | phenoxyethanol | 0.2 | 0.2 | 0.2 | 0.2 | 0.2 | 0.2 |
| | water | 87.5 | 87.0 | 87.6 | 90.8 | 89.8 | 89.8 |
| | Total | 100.0 | 100.0 | 100.0 | 100.0 | 100.0 | 100.0 |
| | pH | 7.2 | 7.3 | 7.1 | 7.2 | 7.2 | 7.2 |
| | Actual active ingredient concentration (%) | approx 1 | approx 1 | approx 1 | | | |
| Evaluations | Precipitation Immediately after preparation | A | A | A | A | A | A |
| | After storage for one month at 40° C. | A | A | A | C | C | C |
| | Storage stability APPS retention rate after storage for one month at 40° C. (%) | 98 | 96 | 98 | 70 | 72 | 72 |

TABLE 1-continued

|  |  | Comparative Example | | | | |
|---|---|---|---|---|---|---|
|  |  | 4 | 5 | 6 | 7 | 8 |
| Composition (% by mass) | APPS | 1 | 1 | 1 | 1 | 1 |
|  | glycerol | 4 | 4 | 4 | 4 | 4 |
|  | 1,3-butylene glycol | 4 | 4 | 4 | 4 | 4 |
|  | lauryl dimethylaminoacetate betaine 26% aqueous solution |  |  |  |  |  |
|  | coconut oil fatty acid amidopropyl dimethylaminoacetate betaine 30% aqueous solution |  |  |  |  |  |
|  | isostearamidopropyl dimethylaminoacetate betaine 31% aqueous solution |  |  |  |  |  |
|  | decaglyceryl monostearate |  |  |  |  |  |
|  | polyoxyethylene (15) glyceryl monostearate |  |  |  |  |  |
|  | polyoxyethylene (20) sorbitan monooleate | 1 |  |  |  |  |
|  | polyoxyethylene (30) sorbitol tetraoleate |  | 1 |  |  |  |
|  | sodium polyoxyethylene (3) lauryl ether sulfate 25% aqueous solution |  |  | 4 |  |  |
|  | cetyl trimethylammonium chloride 30% aqueous solution |  |  |  | 3.3 |  |
|  | sodium laurylaminodipropionate 30% aqueous solution |  |  |  |  | 3.3 |
|  | phenoxyethanol | 0.2 | 0.2 | 0.2 | 0.2 | 0.2 |
|  | water | 89.8 | 89.8 | 86.8 | 87.5 | 87.5 |
|  | Total | 100.0 | 100.0 | 100.0 | 100.0 | 100.0 |
|  | pH | 7.4 | 7.2 | 8.5 | 5.8 | 8.3 |
|  | Actual active ingredient concentration (%) |  |  | approx 1 | approx 1 | approx 1 |
| Evaluations | Precipitation Immediately after preparation | A | A | C | C | C |
|  | After storage for one month at 40° C. | C | C | C | C | C |
|  | Storage stability  APPS retention rate after storage for one month at 40° C. (%) | 73 | 74 | 60 | 55 | 59 |

TABLE 2

|  |  | Example | | | | | | | |
|---|---|---|---|---|---|---|---|---|---|
|  |  | 4 | 5 | 6 | 7 | 8 | 9 | 10 | 11 |
| Composition (% by mass) | APPS | 1 | 1 | 1 | 1 | 1 | 1 | 1 | 1 |
|  | glycerol | 4 | 4 | 4 | 4 | 4 | 4 | 4 | 4 |
|  | 1,3-butylene glycol | 4 | 4 | 4 | 4 | 4 | 4 | 4 | 4 |
|  | lauryl dimethylam inoacetate betaine 26% aqueous solution | 7.7 | 3.8 | 1.9 | 0.38 |  |  |  |  |
|  | coconut oil fatty acid amidopropyl dimethylaminoacetate betaine 30% aqueous solution |  |  |  |  | 6.7 | 3.3 | 1.7 | 0.33 |
|  | methylparaben | 0.2 | 0.2 | 0.2 | 0.2 | 0.2 | 0.2 | 0.2 | 0.2 |
|  | water | 83.1 | 87 | 88.9 | 90.42 | 84.1 | 87.5 | 89.1 | 90.47 |
|  | Total | 100.00 | 100.00 | 100.00 | 100.00 | 100.00 | 100.00 | 100.00 | 100.00 |
|  | pH | 7.2 | 7.2 | 7.3 | 7.3 | 7.2 | 7.3 | 7.3 | 7.3 |
|  | Actual active ingredient concentration (%) | approx 2 | approx 1 | approx 0.5 | approx 0.1 | approx 2 | approx 1 | approx 0.5 | approx 0.1 |
| Evaluations | Precipitation Immediately after preparation | A | A | A | A | A | A | A | A |
|  | After storage for one month at 40° C. | A | A | A | B | A | A | A | B |
|  | Storage stability  APPS retention rate after storage for one month at 40° C. (%) | 99 | 98 | 98 | 94 | 96 | 96 | 97 | 93 |

In Tables 1 and 2, the values for pH and the actual active ingredient concentration refer to values measured using the procedures described below.

pH: The pH values (25° C.) of the prepared lotions and milky lotions were measured using the glass electrode method.

A pH meter (F-52 manufactured by Horiba, Ltd.) was used for the pH measurements.

Actual active ingredient concentration: The actual active ingredient concentration (% by mass) of the betaine-type amphoteric surfactant in the lotion was measured by liquid chromatography mass analysis under the measurement conditions listed below.

(Liquid Chromatography Mass Analysis Measurement Conditions)

Column: Shodex C18M 4D (product name), manufactured by Showa Denko K.K.

Column temperature: 40° C.

Eluent: 0.01 M aqueous solution of ammonium acetate/acetonitrile (gradient)

Flow rate: 1.0 mL/minute

Detection: UV 200 to 400 nm (photodiode array)

Ionization method: Electrospray ionization

Among the components shown in Tables 1 and 2, the compounds listed below were used for the betaine-type amphoteric surfactant represented by the above general formula (1), the betaine-type amphoteric surfactant represented by the above general formula (2), and the other surfactants.

[Betaine-Type Amphoteric Surfactant Represented by General Formula (1)]

Lauryl dimethylaminoacetate betaine, 26% aqueous solution: Amphitol 24B, manufactured by Kao Corporation.

[Betaine-Type Amphoteric Surfactants Represented by General Formula (2)]

Coconut oil fatty acid amidopropyl dimethylaminoacetate betaine, 30% aqueous solution: Amphitol 55AB, manufactured by Kao Corporation.

Isostearamidopropyl dimethylaminoacetate betaine, 31% aqueous solution: Obazoline ISAB, manufactured by Toho Chemical Industry Co., Ltd.

[Other Surfactants]

Decaglyceryl monostearate: Nikkol Decaglyn 1-SV, manufactured by Nikko Chemicals Co., Ltd.

Polyoxyethylene (15) glyceryl monostearate: Nikkol TMGS-15, manufactured by Nikko Chemicals Co., Ltd.

Polyoxyethylene (20) sorbitan monooleate: Nikkol TO-10V, manufactured by Nikko Chemicals Co., Ltd.

Polyoxyethylene (30) sorbitol tetraoleate: Nikkol GO-430NV, manufactured by Nikko Chemicals Co., Ltd.

Sodium polyoxyethylene (3) lauryl ether sulfate, 25% aqueous solution: Emal 20C, manufactured by Kao Corporation.

Cetyl trimethylammonium chloride, 30% aqueous solution: Quartamin 60W, manufactured by Kao Corporation.

Sodium laurylaminodipropionate, 30% aqueous solution: Deriphat 160C, manufactured by Cognis Japan Ltd.

Based on the evaluation results for precipitation and storage stability shown in Table 1, it was evident that examples 1 to 3, in which the betaine-type amphoteric surfactant represented by the aforementioned general formula (1) or (2) was formulated, exhibited improved stability of the APPS in the lotion and suppressed generation of precipitates over time in comparison with comparative example 1, in which no surfactant was formulated, and comparative examples 2 to 8, in which other surfactants were formulated.

Further, based on the evaluation results for precipitation and storage stability shown in Table 2, it was evident that, in a similar manner to that observed for examples 1 to 3, examples 4 to 11, in which the betaine-type amphoteric surfactant represented by the aforementioned general formula (1) or (2) was formulated, exhibited improved stability of the APPS in the lotion and suppressed generation of precipitates over time.

The invention claimed is:

1. A skin external preparation comprising an ascorbic acid-2-phosphate derivative, characterized in that
only a sodium ascorbic acid-2-phosphate-6-palmitate is formulated as the ascorbic acid-2-phosphate derivative, and
the skin external preparation further comprises at least one betaine-type amphoteric surfactant selected from the group consisting of compounds represented by a general formula (1) or (2) shown below:

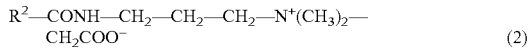

wherein $R^1$ represents a linear or branched alkyl group of 10 to 30 carbon atoms, and $R^2$ represents a linear or branched alkyl group of 8 to 30 carbon atoms.

2. The skin external preparation according to claim 1, wherein at least one of the betaine-type amphoteric surfactantis a compound of the general formula (1) in which $R^1$ is a linear or branched alkyl group of 12 to 24 carbon atoms.

3. The skin external preparation according to claim 1, wherein at least one of the betaine-type amphoteric surfactantis a compound of the general formula (2) in which $R^2$ is a linear or branched alkyl group of 12 to 24 carbon atoms.

4. The skin external preparation according to claim 1, wherein a formulating amount of the sodium ascorbic acid-2-phosphate-6-palmitate is within a range from 0.01 to 10% by mass, relative to a total mass of the skin external preparation.

5. The skin external preparation according to claim 1, wherein an amount of the betaine-type amphoteric surfactant is within a range from 0.1 to 10% by mass, relative to a total mass of the skin external preparation.

6. The skin external preparation according to claim 1, wherein a pH of the skin external preparation is within a range from 6.5 to 7.5.

7. The skin external preparation according to claim 1, wherein the skin external preparation is a cosmetic material.

8. A method of producing a skin external preparation comprising an ascorbic acid-2-phosphate derivative, the method comprising:
formulating: only a sodium ascorbic acid-2-phosphate-6-palmitate as the ascorbic acid-2-phosphate derivative; and at least one betaine-type amphoteric surfactant selected from the group consisting of compounds represented by a general formula (1) or (2) shown below:

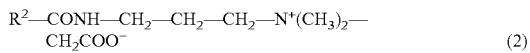

wherein $R^1$ represents a linear or branched alkyl group of 10 to 30 carbon atoms, and $R^2$ represents a linear or branched alkyl group of 8 to 30 carbon atoms.

9. The method according to claim 8, wherein the sodium ascorbic acid-2-phosphate-6-palmitate is formulated in an amount of 0.01 to 10% by mass, relative to a total mass of the skin external preparation.

10. The method according to claim 8, wherein the betaine-type amphoteric surfactant is formulated in an amount of 0.1 to 10% by mass, relative to a total mass of the skin external preparation.

* * * * *